US00PP19534P3

(12) United States Plant Patent
Kleinwee

(10) Patent No.: US PP19,534 P3
(45) Date of Patent: Dec. 2, 2008

(54) ***GERANIUM* PLANT NAMED 'ZONADAROWITE'**

(50) Latin Name: *Pelargonium zonale*
Varietal Denomination: Zonadarowite

(75) Inventor: Theodorus Cornelis Maria van Kleinwee, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 36 days.

(21) Appl. No.: 11/604,929

(22) Filed: Nov. 28, 2006

(65) Prior Publication Data

US 2008/0127387 P1 May 29, 2008

(51) Int. Cl.
*A01H 5/00* (2006.01)

(52) U.S. Cl. ..... Plt./325
(58) Field of Classification Search ..... Plt./325
See application file for complete search history.

(56) References Cited

PUBLICATIONS

UPOVROM Plant Variety database PBR 20051216 search for cultivar Zonadarowite.*

* cited by examiner

*Primary Examiner*—Annette H Para
(74) *Attorney, Agent, or Firm*—S. Matthew Edwards

(57) ABSTRACT

A new *Geranium* plant, particularly distinguished by the dark rose flower color with a white spot in the center of the flower, compact to medium vigorous plant type, and green foliage with little zone.

1 Drawing Sheet

Latin name of the genus and species of the plant claimed: *Pelargonium zonale* (*L*)*L'Hérit ex Ait.*
Varietal denomination: 'Zonadarowite'.

BACKGROUND OF THE NEW PLANT

The present invention comprises a new *Geranium*, botanically known as *Pelargonium zonale* (*L.*)*L'Hérit. ex Ait*, and hereinafter referred to by the variety name 'Zonadarowite.'

'Zonadarowite' is a product of a planned breeding program. The new cultivar 'Zonadarowite' has large, semi-double flowers, is relatively vigorous, but with a well-branched growth habit, and has good heat resistance.

'Zonadarowite' originates from a hybridization in a controlled breeding program in Enkhuizen, The Netherlands. The female parent was an unpatented hybrid seedling identified as 'T023' with dark lavender color, long flower stem, and big umbel. The male parent of 'Zonadarowite' was an unpatented hybrid seedling identified as 'J2221- 4' with light lavender color, very late flowering, and big umbels.

'Zonadarowite' was selected as one flowering plant within the progeny of the stated cross in 2000 in a controlled environment in Enkhuizen, The Netherlands.

The first act of asexual reproduction of 'Zonadarowite' was accomplished when vegetative cuttings were taken from the initial selection in the Fall of 2000 in a controlled environment in Enkhuizen, the Netherlands.

Horticultural examination of plants grown from cuttings of the plant initiated in April of 2001 in Enkhuizen, The Netherlands, and continuing thereafter, has demonstrated that the combination of characteristics as herein disclosed for 'Zonadarowite' are firmly fixed and are retained through successive generations of asexual reproduction. 'Zonadarowite' has not been observed under all possible environmental conditions. The phenotype may vary significantly with variations in environment such as temperature, light intensity and day length.

BRIEF DESCRIPTION OF THE NEW VARIETY

The accompanying photographic drawing shows typical flower and foliage characteristics of 'Zonadarowite' with colors being as true as possible with an illustration of this type. The photographic drawing shows a flowering potted plant of the new variety.

DETAILED BOTANICAL DESCRIPTION

The measurements were taken in Enkhuizen, Netherlands, in August 2005 on 26 week old plants that were growing in window boxes. Culture of these plants started mid February, 2005 in the greenhouse; plants were transferred to window boxes mid May, 2005.

BRIEF SUMMARY OF INVENTION

The following observations, measurements, and comparisons describe plants grown outside in Enkhuizen, The Netherlands. The following traits have been repeatedly observed and are determined to be basic characteristics of the new variety. The combination of these characteristics distinguishes this *Geranium* as a new and distinct variety.

Color references are primarily to the R.H.S. Colour Chart of The Royal Horticultural Society of London.

Plants of the new *Geranium* differ primarily from the plants of the female parent 'T023' in the following characteristics:

The plants of the female parent 'T023' have a darker lavender color, a longer flower stem, and bigger umbels with smaller flowers than plants of the new *Geranium*.

Plants of the new *Geranium* differ primarily from the plants of the male parent 'J2221 - 4' in the following characteristics:

The plants of the male parent 'J2221-4' have a lighter lavender color, are later flowering, and have bigger umbels and are more vigorous than plants of the new *Geranium*.

TABLE 1

DIFFERENCES BETWEEN THE NEW VARIETY 'ZONADAROWITE' AND A SIMILAR VARIETY

| | 'Zonadarowite' | 'Klegany' (U.S. Plant Pat. No. 9,110) |
|---|---|---|
| Leaf color (upper side) | 137B | 146A |
| Internode length | Very short | Long |
| Flower color (Upper side of upper petal) | top 66A, fading to mid section to 67B, base 155D | N66A with blotch 53C, base 155D |

Plant:
*Plant height* (*cm*).—17.
*Plant height* (*inflorescence included*) (*cm*).—27.
*Plant width* (*cm*).—35.
*Plant shape.*—Round.

Foliage:
*Length* (*cm*).—6.
*Width* (*cm*).—9.
*Shape.*—Reniform.
*Base shape*—Hastate.
*Base size.* (*cm*).—5.
*Apex shape.*—Very weak lobes.
*Apex size* (*cm*).—4.
*Color of upper surface.*—137B.
*Color of lower surface.*—146A.
*Color of zone.*—139A; Little zone.
*Color of veins.*—146B.
*Margin.*—Bicrenate.
*Petioles length* (*cm*).—5–9.
*Diameter of petiole* (*mm*).—3.
*Leaves smooth and hairy.*—Only at nerves.
*Texture of leaves.*—Upper surface smooth.
*Veins.*—Palmate.

Stem:
*Length of internodes* (*mm*).—10–35.
*Color of stem.*—146B.
*Diameter* (*mm*).—8.

Inflorescence:
*Shape.*—Round outline.
*Diameter* (*cm*).—13.
*Umbel depth* (*cm*).—7.
*Length of peduncle* (*cm*).—18–25.
*Peduncle diameter* (*mm*).—4–5.
*Color of peduncle.*—146B with little 184A.
*Length of pedicel* (*cm*).—2.5–3.5.
*Color of pedicel.*—146D at base, rest 184B.
*Number of flowers per inflorescence.*—60.

Corolla:
*Form.*—Appears semi double.
*Shape.*—Round outline, upper petals about the same size as the lower petals, fringled flower.
*Length of flower* (*cm*).—3.5.
*Width of flower* (*cm*).—4.2.
*Number of petals.*—5–6.
*Length of petals* (*upper/lower*) (*mm*).—Upper 23. Lower 22.
*Width of petals* (*upper/lower*) (*mm*).—Upper 17. Lower 21.
*Shape petals.*—Obovate, base acute, upper end is truncate or rounded, margin is entire.
*Color upper side of upper petals.*—Top 66A, fading to the mid section to 67B; base 155D.
Color lower side of upper petals. —67C to 155
*Color upper side of lower petals.*—67B.
*Color lower side of lower petals.*—67C.
*Number of petaloids.*—2–4; medium size, crumpled.
*Color petaloids.*—67D.
*Fading color when flower starts aging.*—No.
*Duration of flowering.*—Continuous flowering throughout the Summer.

Bud (just before opening):
*Shape.*—Narrow elliptic.
*Shape base of bud.*—Truncate.
*Shape top of bud.*—Acuminate.
*Sepals hairy and smooth.*—Yes.
*Length* (*mm*).—10.
*Width* (*mm*).—4.
*Color.*—146D.
*Number of sepals.*—5.
*Color of sepals.*—146C.
*Length of sepals* (*mm*).—10.
*Width of sepals* (*mm*).—3.

Reproductive organs:
*Number of lobes of stigma.*—5.
*Color stigma.*—63A.
*Length of style* (*mm*).—4.
*Color of style.*—63B.
*Number of anthers.*—7.
*Length of anthers* (*mm*).—3.
*Shape of anthers.*—Ovate.
*Length filaments* (*mm*).—8.
*Color of filaments.*—155D, Top 67B.
*Pollen present.*—Yes.
*Color of pollen.*—32A.
*Fertility/seed set.*—No.

Seed development: No seed development has been observed on plants on the new *Geranium*.

Disease/pest resistance: No disease/pest resistance has been observed to date.

What is claimed is:

1. A new and distinct variety of *Geranium* plant, substantially as illustrated and described herein.

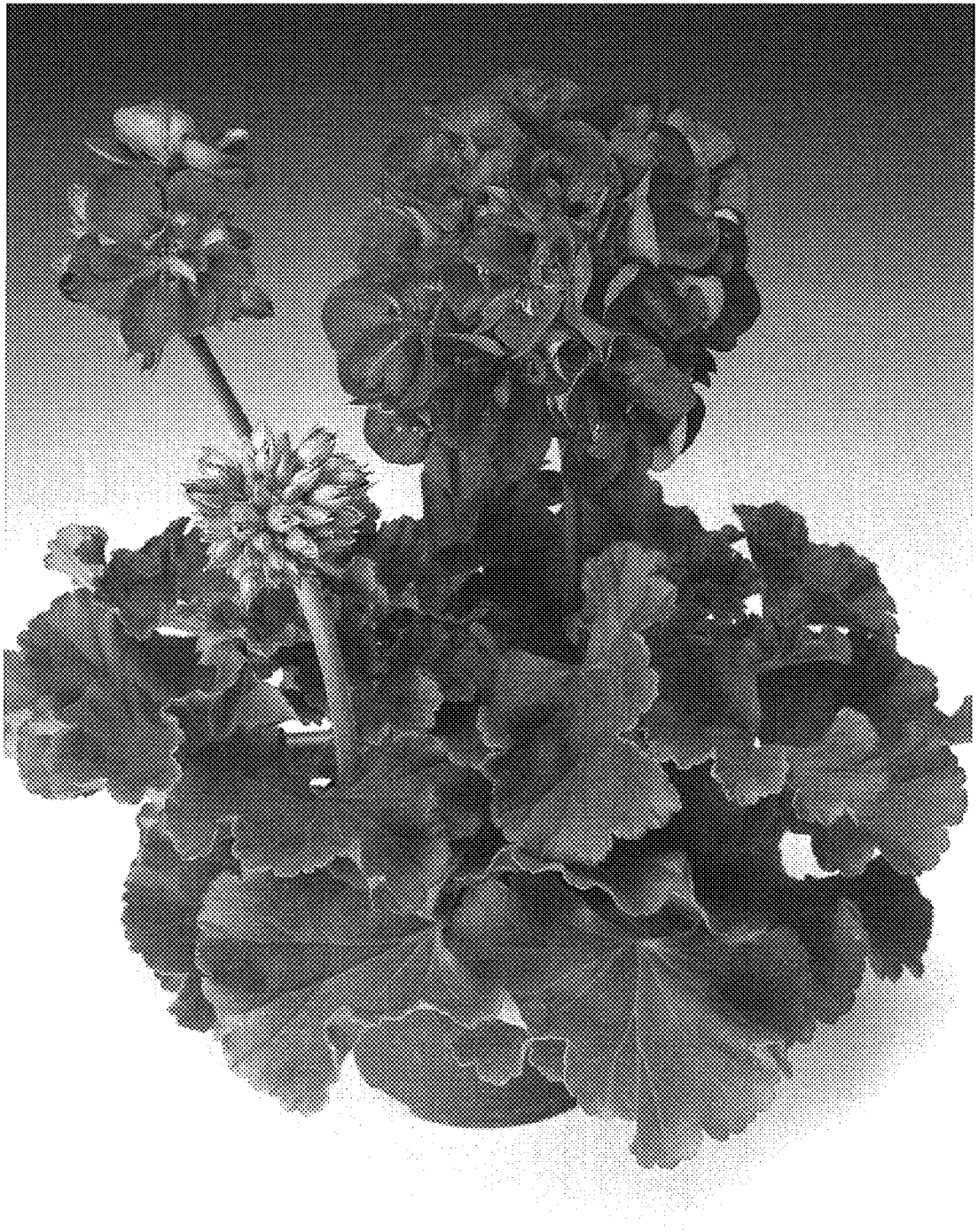

* * * * *